(12) United States Patent
He et al.

(10) Patent No.: US 11,866,459 B2
(45) Date of Patent: Jan. 9, 2024

(54) COCRYSTAL OF PROGESTERONE AND PREPARATION METHOD AND USE THEREOF

(71) Applicant: NATIONAL INSTITUTES FOR FOOD AND DRUG CONTROL, Beijing (CN)

(72) Inventors: Lan He, Beijing (CN); Jing Xiong, Beijing (CN); Xiangxiang Wu, Beijing (CN); Xin Zhu, Beijing (CN); Zhonglin Lu, Beijing (CN); Yan Shi, Beijing (CN); Na Zhang, Beijing (CN); Yang Liu, Beijing (CN)

(73) Assignee: NATIONAL INSTITUTES FOR FOOD AND DRUG CONTROL, Beijing (CN)

( * ) Notice: Subject to any disclaimer, the term of this patent is extended or adjusted under 35 U.S.C. 154(b) by 32 days.

(21) Appl. No.: 17/191,769

(22) Filed: Mar. 4, 2021

(65) Prior Publication Data
US 2021/0277049 A1    Sep. 9, 2021

(30) Foreign Application Priority Data

Mar. 9, 2020   (CN) .......................... 202010160411.2

(51) Int. Cl.
| | |
|---|---|
| *C07J 5/00* | (2006.01) |
| *A61P 15/00* | (2006.01) |
| *A61P 15/06* | (2006.01) |
| *A61P 15/12* | (2006.01) |

(52) U.S. Cl.
CPC ............. *C07J 5/0015* (2013.01); *A61P 15/00* (2018.01); *A61P 15/06* (2018.01); *A61P 15/12* (2018.01); *C07B 2200/13* (2013.01)

(58) Field of Classification Search
CPC ..................... C07J 5/0015; C07B 2200/13
See application file for complete search history.

(56) References Cited

U.S. PATENT DOCUMENTS

| | | | | |
|---|---|---|---|---|
| 7,053,192 B2 * | 5/2006 | Li | ...................... | A61K 31/7052 536/7.4 |
| 7,727,556 B2 | 6/2010 | Barbera et al. | | |
| 2005/0135999 A1 * | 6/2005 | Elomari | ................. | C01B 39/48 423/706 |
| 2007/0032435 A1 * | 2/2007 | Alani | ...................... | A61P 31/12 514/369 |
| 2007/0249544 A1 * | 10/2007 | Himmelsbach | ...... | C07D 407/12 536/4.1 |
| 2008/0004448 A1 * | 1/2008 | Wayne | ..................... | A61P 25/08 546/276.7 |
| 2008/0089835 A1 * | 4/2008 | Burton | ..................... | C01B 39/48 423/706 |
| 2008/0103186 A1 * | 5/2008 | Glover | .............. | A61K 31/4184 514/395 |
| 2008/0139569 A1 * | 6/2008 | Rocco | ..................... | A61P 35/00 544/234 |
| 2008/0319024 A1 * | 12/2008 | Greil | ......................... | A61P 3/04 514/342 |
| 2009/0069281 A1 * | 3/2009 | Austad | .................... | A61P 35/00 514/183 |
| 2009/0124652 A1 * | 5/2009 | Ach | ........................ | A61P 37/02 546/82 |
| 2009/0137794 A1 * | 5/2009 | Mendez | ................... | C07J 43/00 540/78 |
| 2009/0176983 A1 * | 7/2009 | Dova | ..................... | A61P 31/18 544/242 |
| 2009/0203705 A1 * | 8/2009 | Biagetti | .................. | A61P 25/32 514/252.02 |
| 2009/0239946 A1 * | 9/2009 | McKeown | ............. | A61K 33/30 514/502 |
| 2010/0021539 A1 * | 1/2010 | Kowalski | ................ | A61P 19/10 514/342 |

FOREIGN PATENT DOCUMENTS

CN         110078780 A         8/2019

OTHER PUBLICATIONS

Samipillai et al. (Journal of Crystal Growth, 2019, 507, 270-282).*
Abosede et al. (Crystal Growth and Design, 2012, 36(10), 1969-1977).*

* cited by examiner

*Primary Examiner* — Susanna Moore
(74) *Attorney, Agent, or Firm* — Ballard Spahr LLP

(57) ABSTRACT

The present invention relates to a cocrystal of progesterone, which is formed by the active ingredient progesterone and a cocrystal former which is selected from isophthalic acid, 4-formylbenzeneboronic acid and 3-nitrophthalic acid. The present invention also relates to the method for preparing the cocrystal of progesterone and use thereof for increasing the thickness of endometrium, improving progesterone's solubility or increasing progesterone's permeation rate.

11 Claims, 11 Drawing Sheets

COCRYSTAL OF PROGESTERONE AND PREPARATION METHOD AND USE THEREOF

CROSS-REFERENCE TO RELATED APPLICATIONS

This application claims priority to Chinese Application No. 202010160411.2, filed Mar. 9, 2020, which Chinese Application is hereby incorporated by reference in its entirety.

TECHNICAL FIELD

The present invention belongs to the technical field of cocrystals of organic drugs, and specifically discloses a cocrystal of progesterone, a method for preparing the same and use thereof.

BACKGROUND ART

Progesterone has a chemical name of pregn-4-ene-3,20-dione, a molecular formula of $C_{21}H_{30}O_2$, and a structural formula shown in formula a below. Progesterone belongs to a kind of natural progestins drug, and is a major progestin with biological activity secreted by the ovaries. Progesterone is hardly soluble in water and poorly absorbed by the body, and has a strong first-pass effect when taken orally. Thus, it is generally administered by injection in clinical practice. Since the treatment with progesterone often requires long-term administration, injection administration brings some inconvenience to patients. In addition, progesterone injection is an oil solution, and long-term administration thereof will cause topical redness, induration or even abscess at the administration site.

Isophthalic acid has a molecular formula of $C_8H_6O_4$ and a structural formula as shown in formula b below. 4-formylbenzeneboronic acid has a molecular formula of $C_7H_7BO_3$ and a structural formula as shown in formula c below. 3-nitrophthalic acid has a molecular formula of $C_8H_5NO_6$ and a structural formula as shown in formula d below.

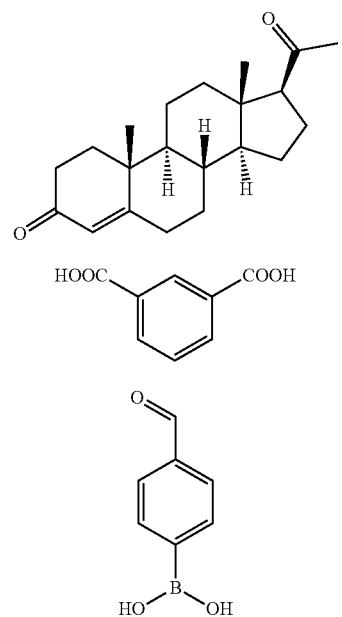

a b c

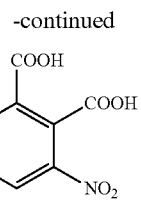

d

A pharmaceutical cocrystal refers to a new crystal formed by assembling an active pharmaceutical ingredient and a cocrystal former in a certain ratio by hydrogen bonds or non-covalent bonds with saturation and directionality, with all the components present in a fixed stoichiometric ratio. The cocrystal formed from a drug generally maintains the properties of the drug itself.

SUMMARY OF THE INVENTION

The purpose of the present invention is to provide a novel cocrystal of progesterone, a method for preparing the same and use thereof.

The purpose of the present invention is achieved through the following technical solutions.

A first aspect of the present invention relates to a cocrystal of progesterone, which is formed by the active ingredient progesterone and a cocrystal former which is selected from isophthalic acid, 4-formylbenzeneboronic acid and 3-nitrophthalic acid.

In a preferred embodiment, progesterone and the cocrystal former in the cocrystal of progesterone are present in a molar ratio of 1:3 to 3:1, preferably 1:2 to 2:1.

In a preferred embodiment, progesterone is connected to the cocrystal former via hydrogen bonds.

In a preferred embodiment, the X-ray diffraction characteristics of the cocrystal of progesterone are as follows.

(1) Where the cocrystal former is isophthalic acid, a progesterone-isophthalic acid cocrystal is obtained, wherein the progesterone-isophthalic acid cocrystal belongs to a triclinic system with a space group of P1 and unit cell parameters of a=21.889(6) Å, b=7.4735(17) Å, c=16.423(4) Å, α=γ=90°, β=125.052(14), V=2199.3(9) Å³ and Z=4; $\rho_{calc}g$=1.228 cm³; µ=0.083 mm⁻¹; F(000)=880; radiation of Mo-Kα; 2θ range of 1.51° to 27.51°; index ranges of −28≤h≤28, −9≤k≤9 and −20≤l≤21; reflections collected=14151; unique reflections, Rint=4693, 0.2434; unique reflections data/restraints/parameters=4693/5/277; goodness-of-fit (GOF)=0.912; $R_1$[I>2(I)]=0.0677; $wR_2$(all)=0.2780; and largest difference peak/hole=0.725/−0.801 e Å⁻³; and powder X-ray diffraction characteristic peaks of the progesterone-isophthalic acid cocrystal, expressed as 2θ angles, appear at 6.56°±0.2°, 10.96°±0.2°, 13.14°±0.2°, 16.17°±0.2°, 19.76°±0.2°, 20.32°±0.2°, 21.04°±0.2°, 22.20°±0.2°, 24.17°±0.2°, 26.45°±0.2°, 28.05°±0.2°, and 28.55°±0.2°.

(2) Where the cocrystal former is 4-formylbenzeneboronic acid, a progesterone-4-formylbenzeneboronic acid cocrystal was obtained, wherein the progesterone-4-formylbenzeneboronic acid cocrystal belongs to an orthorhombic system with a space group of $P2_12_12_1$, and unit cell parameters of a=9.2744(17)Å, b=14.001(3)Å, c=19.632(4)Å, α=β=γ=90°, V=2549.2(8)Å³ and Z=4; $\rho_{calc}g$=1.215 cm³; µ=0.081 mm⁻¹; F(000)=1000; radiation of Mo-Kα; 2θ range of 3.35° to 27.50°; index ranges of −12≤h≤10, −18≤k≤18 and −25≤l≤21; reflections collected=17964; unique reflections, Rint=5828, 0.0488; unique reflections data/restraints/parameters=5828/0/311; goodness-of-fit (GOF)=0.918;

$R_1[I>2(I)]=0.0476$; $wR_2(a11)=0.1281$; largest difference peak/hole=0.144/−0.147 e Å$^{-3}$; and powder X-ray diffraction characteristic peaks of the progesterone-4-formylbenzeneboronic acid cocrystal, expressed as 2θ angles, appear at 9.04°±0.2°, 10.55°±0.2°, 12.64°±0.2°, 13.44°±0.2°, 15.53°±0.2°, 16.48°±0.2°, 16.99°±0.2°, 18.22°±0.2°, 19.11°±0.2°, 19.66°±0.2°, 20.70°±0.2°, 21.18°±0.2°, 22.12°±0.2°, 23.48°±0.2°, 24.68°±0.2°, 26.63°±0.2°, and 27.85°±0.2°.

(3) Where the cocrystal former is 3-nitrophthalic acid, a progesterone-3-nitrophthalic acid cocrystal is obtained, wherein the progesterone-3-nitrophthalic acid cocrystal belongs to an orthorhombic system with a space group of $P2_12_12_1$, and unit cell parameters of a=7.7804(8)Å, b=15.6533(15)Å, c=22.414(2)Å, α=β=γ=90°, V=2729.8(5) Å$^3$ and Z=4; $\rho_{calc}g$=1.323 cm$^3$; μ=0.098 mm$^{-1}$; F(000)=1160; radiation of Mo-Kα; 2θ range of 1.59° to 25.44°; index ranges of −8≤h≤9, −18≤k≤18 and −27≤l≤23; reflections collected=14423; unique reflections, Rint=5036, 0.0304; unique reflections data/restraints/parameters=5036/3/366; goodness-of-fit (GOF)=1.004; $R_1[I>2(I)]$=0.0409; $wR_2(a11)$=0.1101; and largest difference peak/hole=0.226/−0.223 e Å$^{-3}$; and powder X-ray diffraction characteristic peaks of the progesterone-3-nitrophthalic acid cocrystal, expressed as 2θ angles, appear at 9.08°±0.2°, 13.01°±0.2°, 13.39°±0.2°, 13.78°±0.2°, 15.88°±0.2°, 16.55°±0.2°, 18.78°±0.2°, 19.29°±0.2°, 20.87°±0.2°, 23.34°±0.2°, 26.27°±0.2°, 27.33°±0.2°, and 29.79°±0.2°.

A second aspect of the present invention relates to a method for preparing the cocrystal of progesterone according to the first aspect of the present invention. This method is a slow solvent evaporation method and comprises the following steps: mixing progesterone and the cocrystal former in proportion, adding a solvent and stirring at 0 to 80° C. for 30 to 360 min until a completely clear solution is obtained, then allowing the solution to stand at room temperature for 3 to 15 days to volatilize the solvent and precipitate crystals, and obtaining a cocrystal of progesterone after filtrating and drying.

In a preferred embodiment, the temperature is 10° C. to 70° C., preferably 30° C. to 70° C., more preferably 40° C. to 60° C.; the stirring time is 30 to 300 min, preferably 40 to 240 min, more preferably 50 to 180 min; and the standing time is 3 to 13 days, preferably 4 to 11 days, more preferably 5 to 9 days.

A third aspect of the present invention relates to a method for preparing the cocrystal of progesterone according to the first aspect of the present invention. This method is a solvent-assisted grinding method and comprises the following steps: mixing progesterone and the cocrystal former in proportion and placing them in a mortar, adding a solvent dropwise and performing grinding, continuously adding an additional solvent during grinding, and after grinding for 10 to 300 min at a temperature of 10° C. to 50° C., performing drying in a vacuum drying cabinet at 40° C. to 80° C. to obtain a cocrystal of progesterone. This method uses the kinetic advantage of solvent-assisted grinding for promoting the formation of cocrystals, improve the mobility between the molecules of solids, and accelerate the formation rate of cocrystals.

In a preferred embodiment, the temperature during grinding is 15° C. to 45° C., preferably 20° C. to 40° C., more preferably 25° C. to 35° C.; the grinding time is 30 to 260 min, preferably 40 to 220 min, more preferably 50 to 160 min; and the temperature in the vacuum drying cabinet is 45° C. to 75° C., preferably 50° C. to 70° C., more preferably 55° C. to 65° C.

In a preferred embodiment, the solvent used in the above two methods is one or a mixture of more of methanol, ethanol, n-propanol, n-butanol, isopropanol, tert-butanol, n-hexanol, ethylene glycol, acetonitrile, acetone, n-hexane or water, wherein the mixture of more of the solvents can be formed by combining two or more of the solvents in different ratios.

In a preferred embodiment, progesterone and the cocrystal former used in the above two methods are present in a molar ratio of 1:3 to 3:1, preferably 1:2 to 2:1.

The preparation method of the invention, cleverly based on the theory of supramolecular chemistry and the principle of crystal engineering, leads to the formation of a cocrystal by using isophthalic acid, 4-formylbenzeneboronic acid or 3-nitrophthalic acid as the cocrystal former, in combination with the characteristics of the molecular structure of progesterone which involves two carbonyl groups as hydrogen bond acceptor groups.

A fourth aspect of the present invention relates to use of the cocrystal of progesterone according to the first aspect of the present invention for increasing the thickness of endometrium, thereby protecting women's endometrium.

A fifth aspect of the present invention relates to use of the cocrystal of progesterone according to the first aspect of the present invention for improving the solubility of progesterone.

A sixth aspect of the present invention relates to use of the cocrystal of progesterone according to the first aspect of the present invention for increasing the permeation rate of progesterone, thereby improving the bioavailability of progesterone and its clinical treatment effect.

The present invention has the following advantages:

(1) The cocrystals of progesterone of the present invention overcome the defects of existing progesterone preparations, can improve the solubility of progesterone, increase the permeation rate of progesterone, and thereby improve the bioavailability of progesterone and its clinical therapeutic effect. The cocrystal of progesterone can be effectively used to increase the thickness of endometrium; protect women's endometrium; prevent miscarriage; treat menopausal syndrome, and thus improve life quality of menopausal women, having good economic and social benefits.

(2) The methods for preparing the cocrystals of progesterone of the present invention are simple, environment-friendly and good in repeatability.

BRIEF DESCRIPTION OF DRAWINGS

FIG. 1-2 shows the powder X-ray diffraction (PXRD) pattern of the monomers of and the cocrystal of progesterone and isophthalic acid, and shows the single-crystal simulated (SC simulated) PXRD pattern of the cocrystal.

FIG. 1-3 shows the differential scanning calorimetry (DSC) pattern of the monomers of and the cocrystal of progesterone and isophthalic acid.

FIG. 1-4 shows the dynamic vapour sorption (DVS) spectrum of the cocrystal of progesterone and isophthalic acid.

FIG. 2-1 shows the IR spectrum of the monomers of and the cocrystal of progesterone and 4-formylbenzeneboronic acid.

FIG. 2-2 shows the PXRD pattern of the monomers of and the cocrystal of progesterone and 4-formylbenzeneboronic acid, and shows the SC simulated PXRD pattern of the cocrystal.

FIG. 2-3 shows the DSC pattern of the monomers of and the cocrystal of progesterone and 4-formylbenzeneboronic acid.

FIG. 2-4 shows the DVS spectrum of the cocrystal of progesterone and 4-formylbenzeneboronic acid.

FIG. 3-1 shows the IR spectrum of the monomers of and the cocrystal of progesterone and 3-nitrophthalic acid.

FIG. 3-2 shows the PXRD pattern of the monomers of and the cocrystal of progesterone and 3-nitrophthalic acid, and the SC simulated PXRD pattern of the cocrystal.

FIG. 3-3 shows the DSC pattern of the monomers of and the cocrystal of progesterone and 3-nitrophthalic acid.

FIG. 3-4 shows the DVS spectrum of the cocrystal of progesterone and 3-nitrophthalic acid.

FIG. 4 shows the DVS spectrum of the progesterone monomer.

Figure 1:
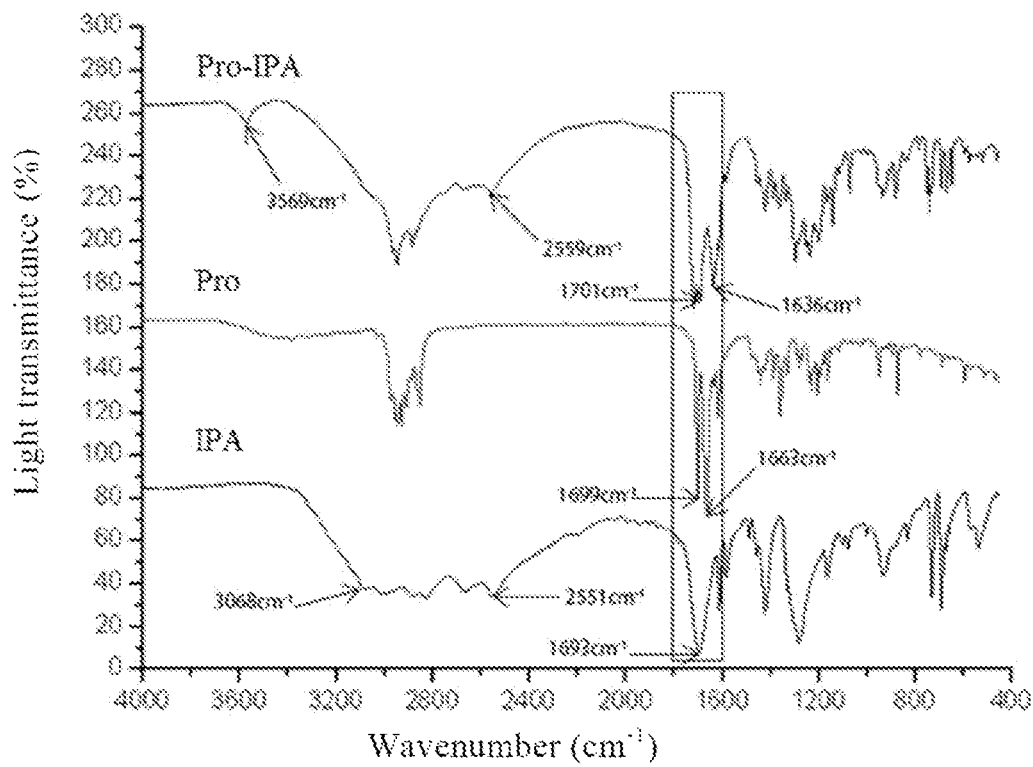
FIG. 1-1 shows the infrared (IR) absorption spectrum of the monomers of and the cocrystal of progesterone and isophthalic acid.

The abbreviations in the drawings stand for the following terms:

| | |
|---|---|
| Pro | Progesterone |
| IPA | Isophthalic acid |
| BBA | 4-formylbenzeneboronic acid |
| NPA | 3-nitrophthalic acid |
| Pro-IPA | Progesterone-isophthalic acid cocrystal |
| Pro-BBA | Progesterone-4-formylbenzeneboronic acid cocrystal |
| Pro-NPA | Progesterone-nitrophthalic acid cocrystal |
| CM | Cocrystal material |

DETAILED DESCRIPTION OF THE INVENTION

For a better understanding of the present invention, in the following the present invention will be described in detail with regard to the examples and drawings. It should be understood, however, that these examples and drawings are only used for exemplarily describing the present invention and are not intended to limit the invention. Any simple change to the present invention made without departing from the concept of the present invention belongs to the protection scope of the present invention.

In the present invention, all the operations are performed at room temperature and at normal pressure unless otherwise specified.

The present invention involves the following detection instruments:

Single-crystal X-ray diffractometer: Bruker P4, Mo target, \ω scan, 296.15K;

Fourier infrared spectrometer: PerkinElmer Frontier FT/IR Spectrometer, normal temperature, KBr pellets, wavelength of 4000 to 450 $cm^{-1}$;

Powder X-ray diffractometer: Rigaku D/max-25509 kw, CuKα radiation, graphite monochromator;

Differential scanning calorimetry analyzer: Mettler Toledo DSC 822e, heating rate of 10° C./min, nitrogen flow rate of 50 mL/min;

Dynamic vapour sorption analyzer: SMS DVS advantage, 25° C.;

Dissolution apparatus: Tianjin Tianda Tianfa Technology Co., Ltd. RC806D, stirring paddle method;

Drug permeation rate tester: Pion Inc µFlux™.

Example 1

157.2 mg of progesterone and 83.8 mg of isophthalic acid were weighed and mixed, 5 ml of an ethanol-water (volume ratio=1:1) mixed solvent was added and stirred at 60° C. for 40 min until a completely clear solution was obtained, then the solution was allowed to stand at room temperature for 3 days to volatilize the solvent and precipitate crystals, and a cocrystal of progesterone was obtained after filtering and drying. The obtained cocrystal was subjected to single-crystal X-ray diffraction analysis. It crystal data and structural parameters are shown in Table 1, indicating that the obtained crystal is a progesterone-isophthalic acid cocrystal.

Example 2

157.3 mg of progesterone and 75.2 mg of 4-formylbenzeneboronic acid were weighed and mixed, 3 ml of a methanol-ethanol-water (volume ratio=1:1:1) mixed solvent was added and stirred at 70° C. for 30 min until a completely clear solution was obtained, then the solution was allowed to stand at room temperature for 4 days to volatilize the solvent and precipitate crystals, and a cocrystal of progesterone was obtained after filtering and drying. The obtained cocrystal was subjected to single-crystal X-ray diffraction analysis. Its crystal data and structural parameters are shown in Table 1, indicating that the obtained crystal is a progesterone-4-formylbenzeneboronic acid cocrystal.

Example 3

157.2 mg of progesterone and 105.0 mg of 3-nitrophthalic acid were weighed and mixed, 3 ml of an ethanol-water (volume ratio=1:1) mixed solvent was added and stirred at 75° C. for 45 min until a completely clear solution was obtained, then the solution was allowed to stand at room temperature for 5 days to volatilize the solvent and precipitate crystals, and a cocrystal of progesterone was obtained after filtering and drying. The obtained cocrystal was subjected to single-crystal X-ray diffraction analysis. Its crystal data and structural parameters are shown in Table 1, indicating that the obtained crystal is a progesterone-3-nitrophthalic acid cocrystal.

Example 4

Figures 1, 2:
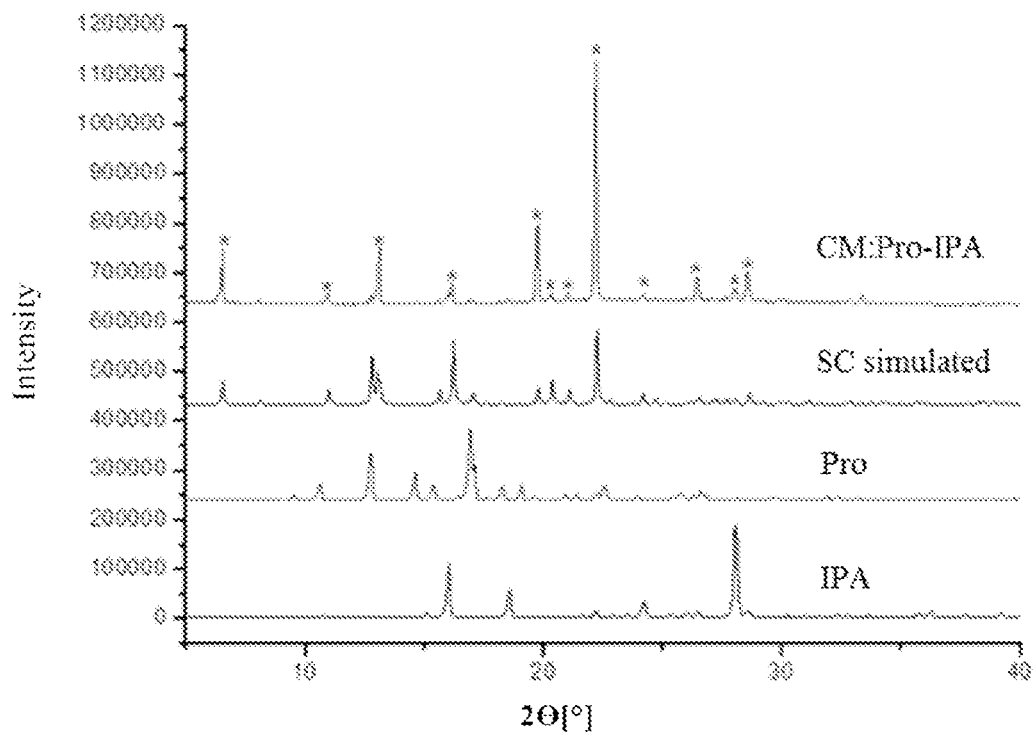

157.2 mg of progesterone and 83.8 mg of isophthalic acid were weighed, mixed and placed in an agate mortar, 50 µl of an ethanol-water (volume ratio=1:1) mixed solvent was added dropwise, grinding was then performed, an additional ethanol-water (volume ratio=1:1) mixed solvent was continuously added during the grinding process, and after grinding was performed for 40 min at room temperature, the solution was dried in a vacuum drying cabinet at 60° C. to obtain a cocrystal of progesterone. The obtained cocrystal was subjected to powder X-ray diffraction analysis. Its diffraction pattern is shown in FIG. 1-2, indicating that the obtained crystal is a progesterone-isophthalic acid cocrystal.

Example 5

157.3 mg of progesterone and 75.2 mg of 4-formylbenzeneboronic acid were weighed, mixed and placed in an agate mortar, 60 μl of a methanol-ethanol-water (volume ratio=1:1:1) mixed solvent was added dropwise, grinding was then performed, an additional methanol-ethanol-water (volume ratio=1:1:1) mixed solvent was continuously added during the grinding process, and after grinding was performed for 30 min at 30° C., the solution was dried in a vacuum drying cabinet at 60° C. to obtain a cocrystal of progesterone. The obtained cocrystal was subjected to powder X-ray diffraction analysis. Its diffraction pattern is shown in FIG. 2-2, indicating that the obtained crystal is a progesterone-4-formylbenzeneboronic acid cocrystal.

Example 6

Figures 1, 2, 3:
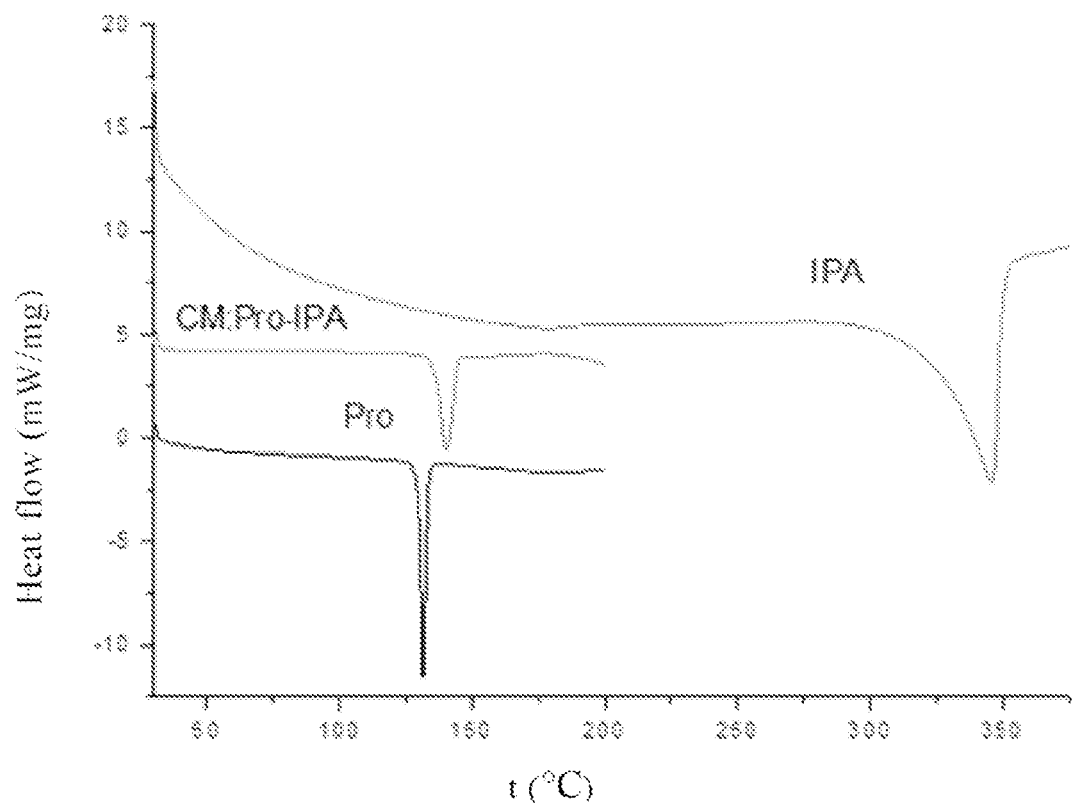
Figures 1, 2, 3, 4:
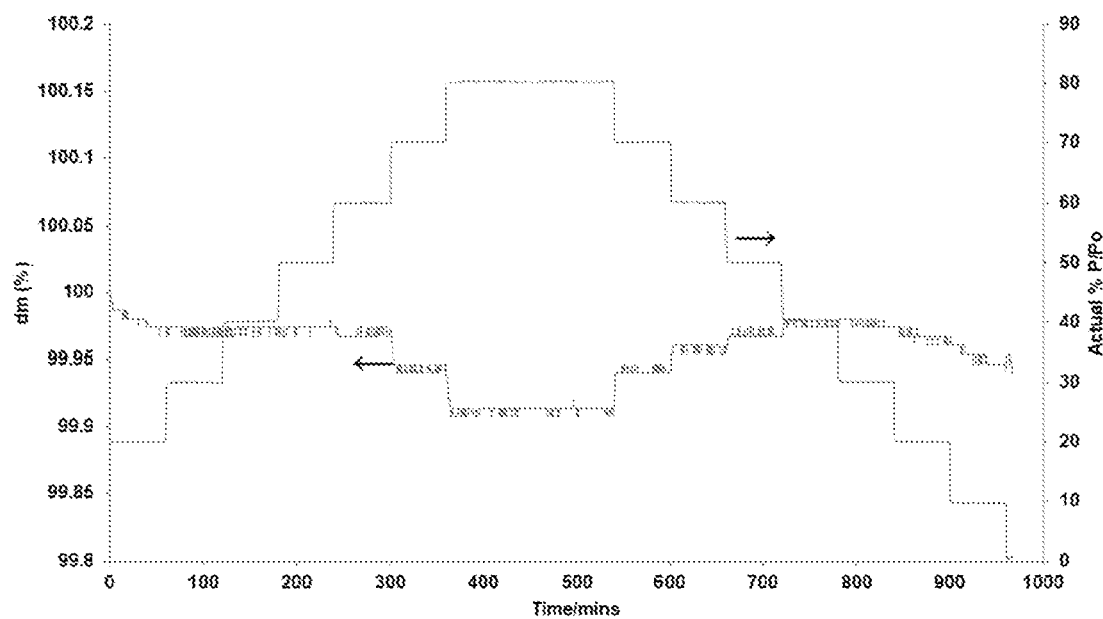
Figures 1, 2:
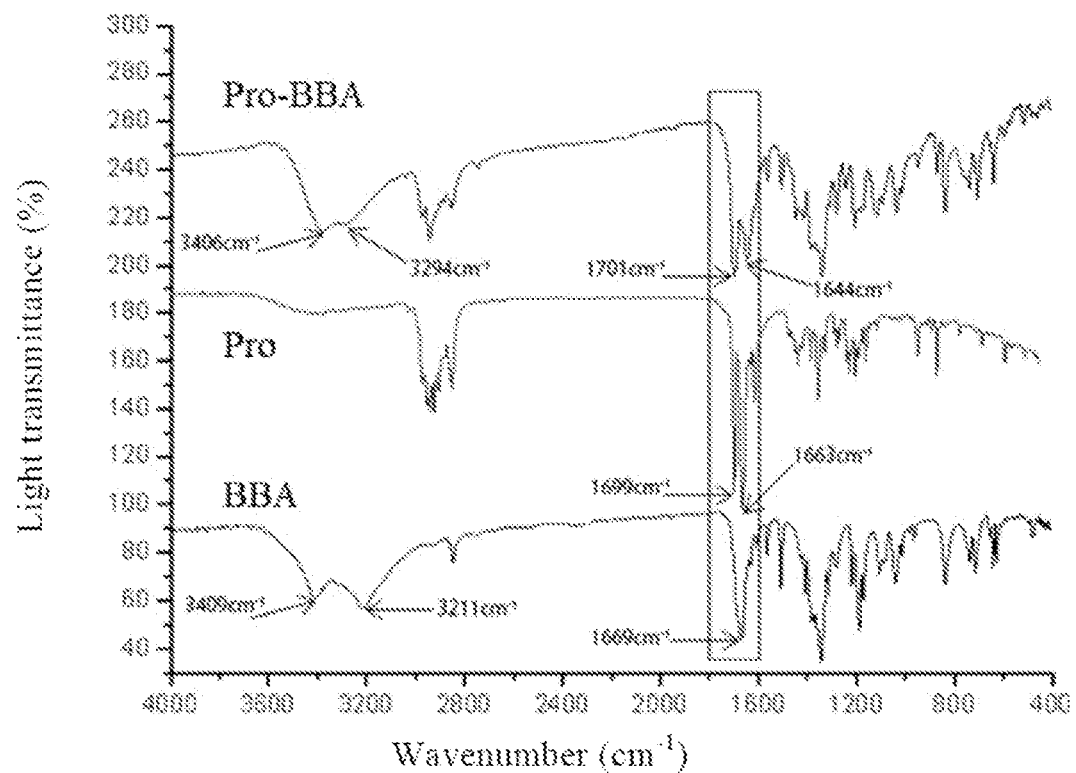
Figure 2:
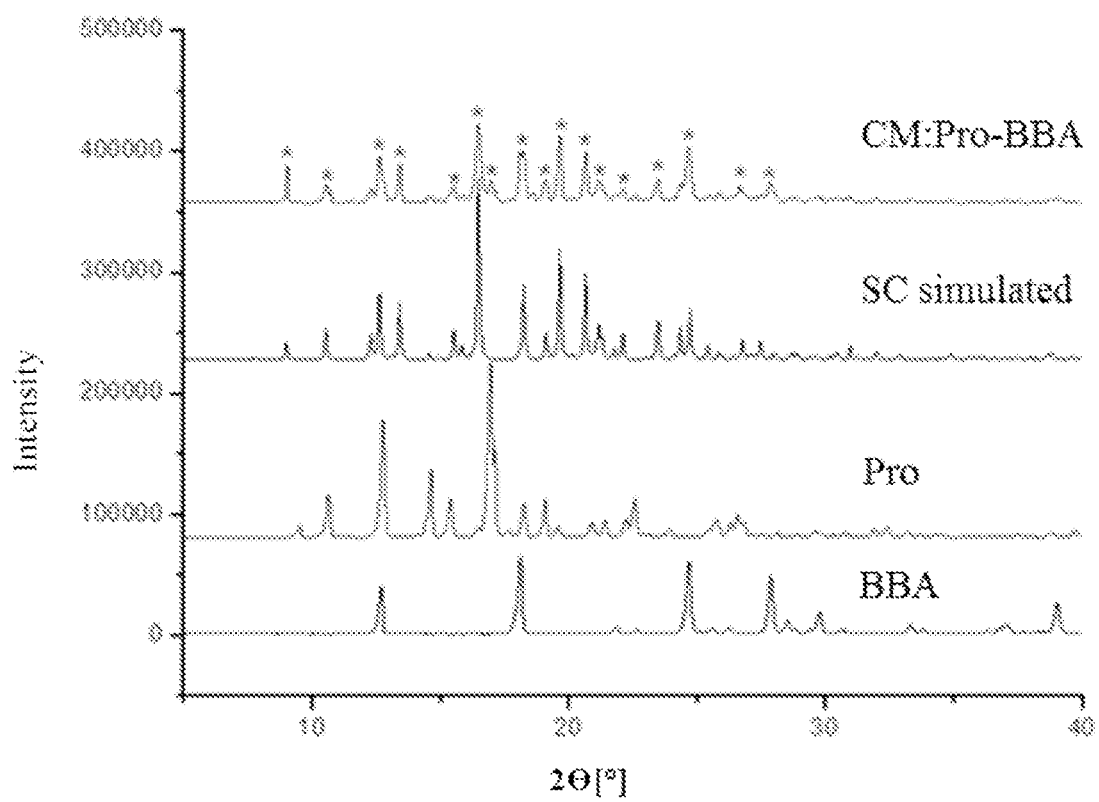
Figures 2, 3:
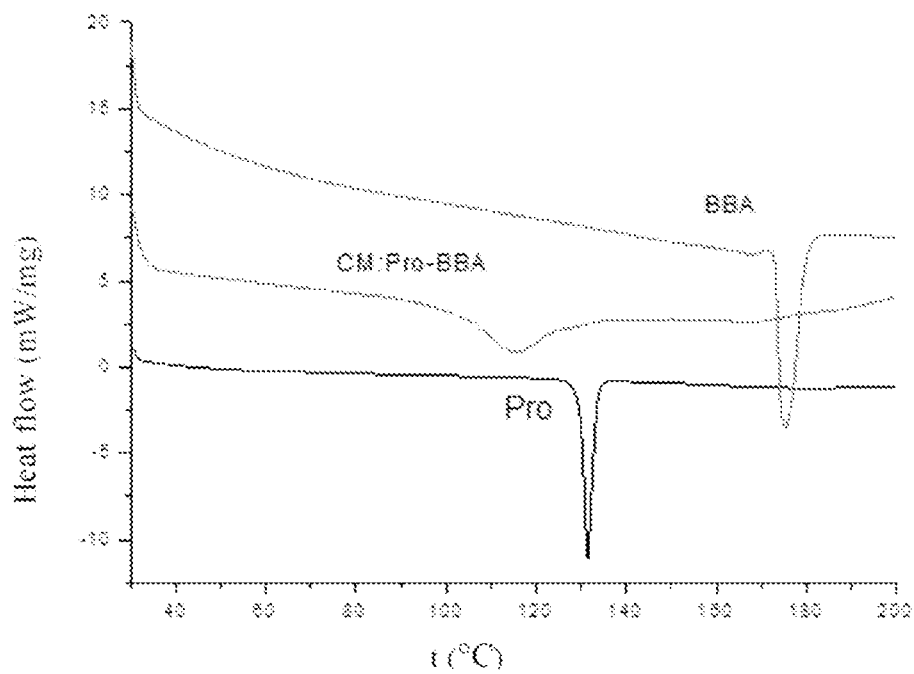
Figures 2, 3, 4:
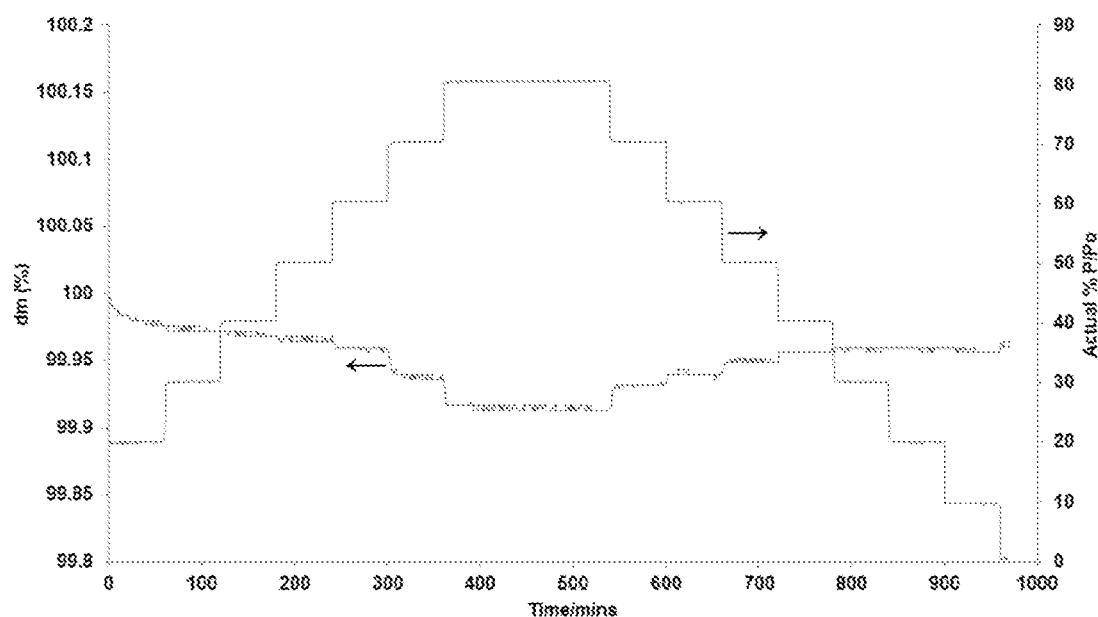
Figures 1, 3:
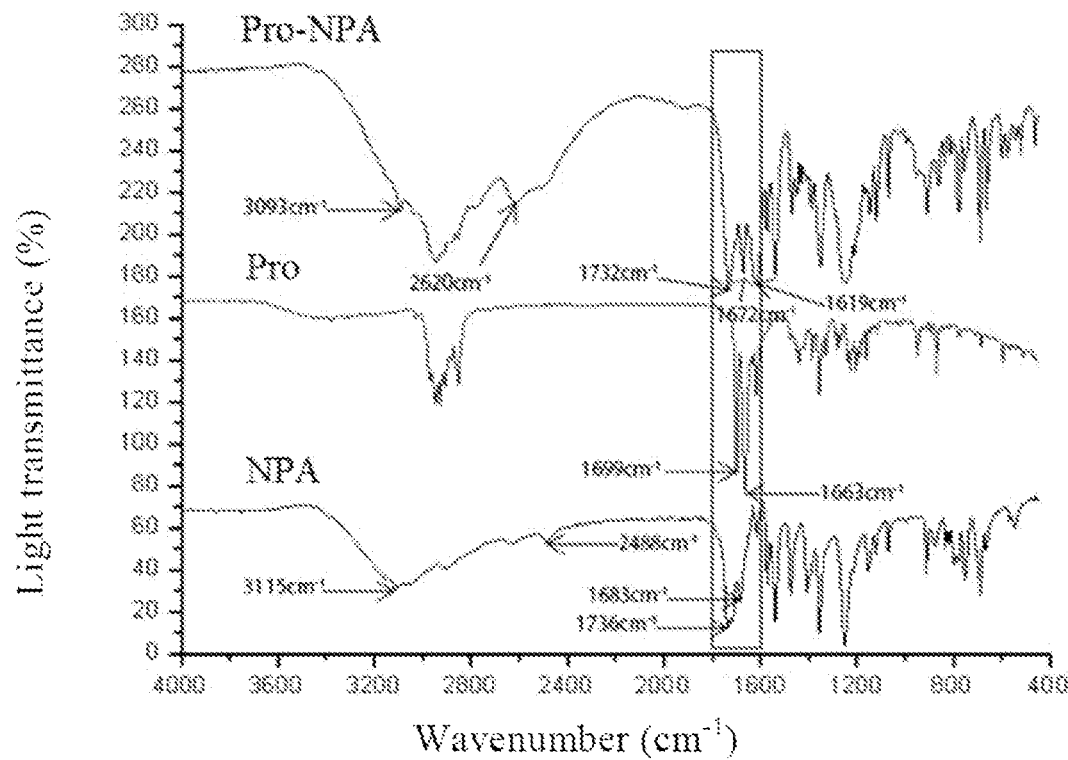
Figures 2, 3:
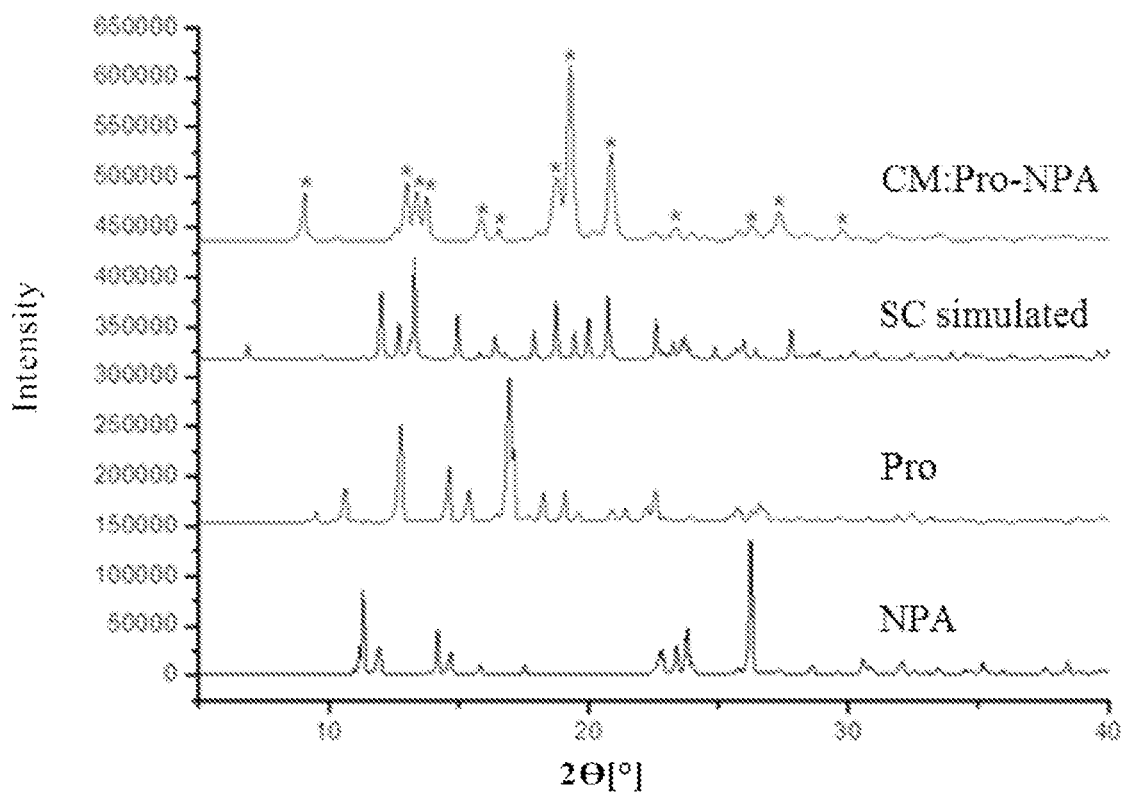
Figure 3:
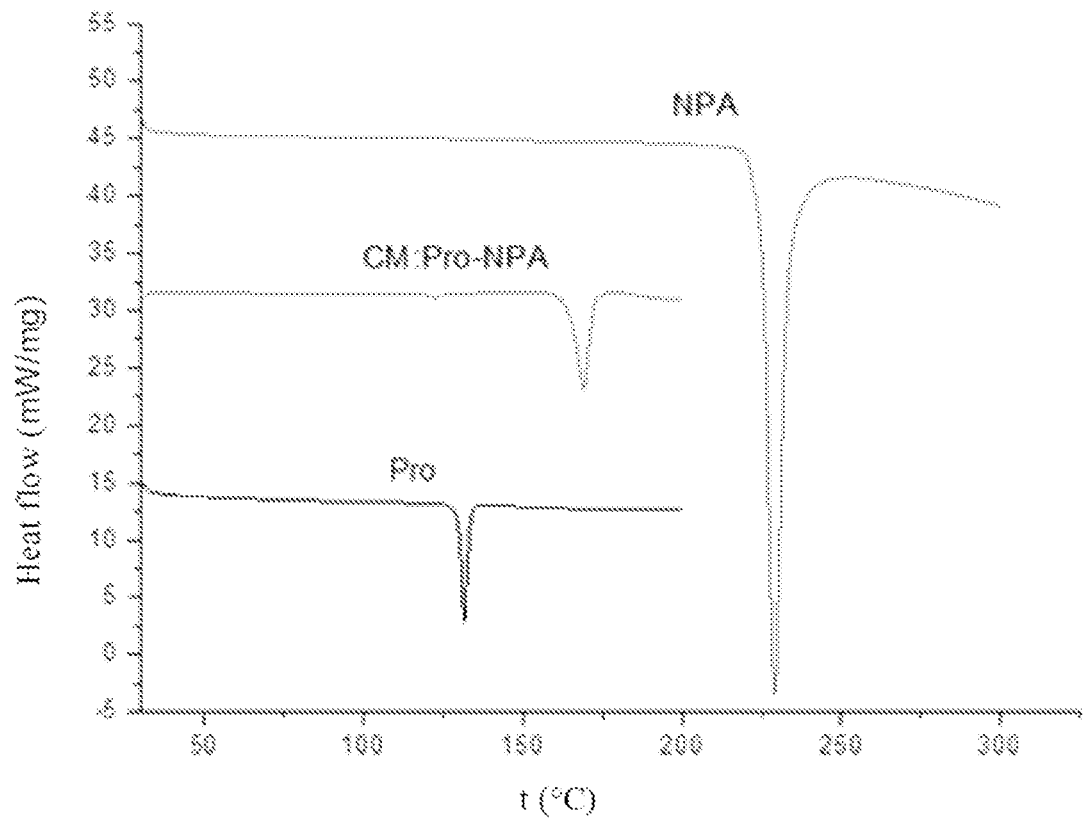
Figures 3, 4:
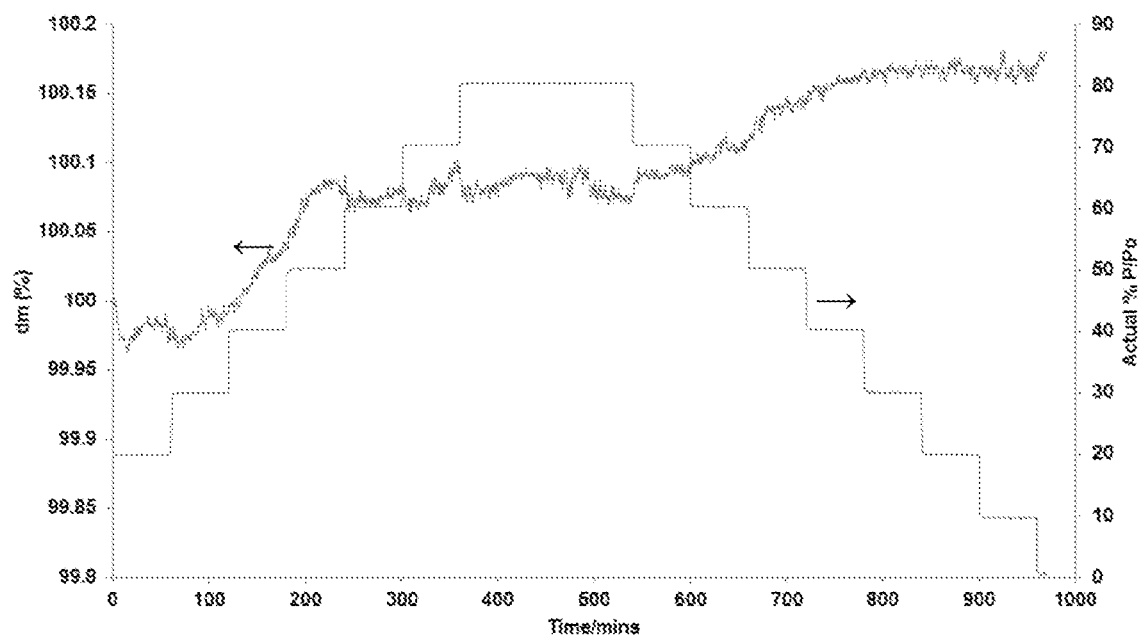
Figure 4:
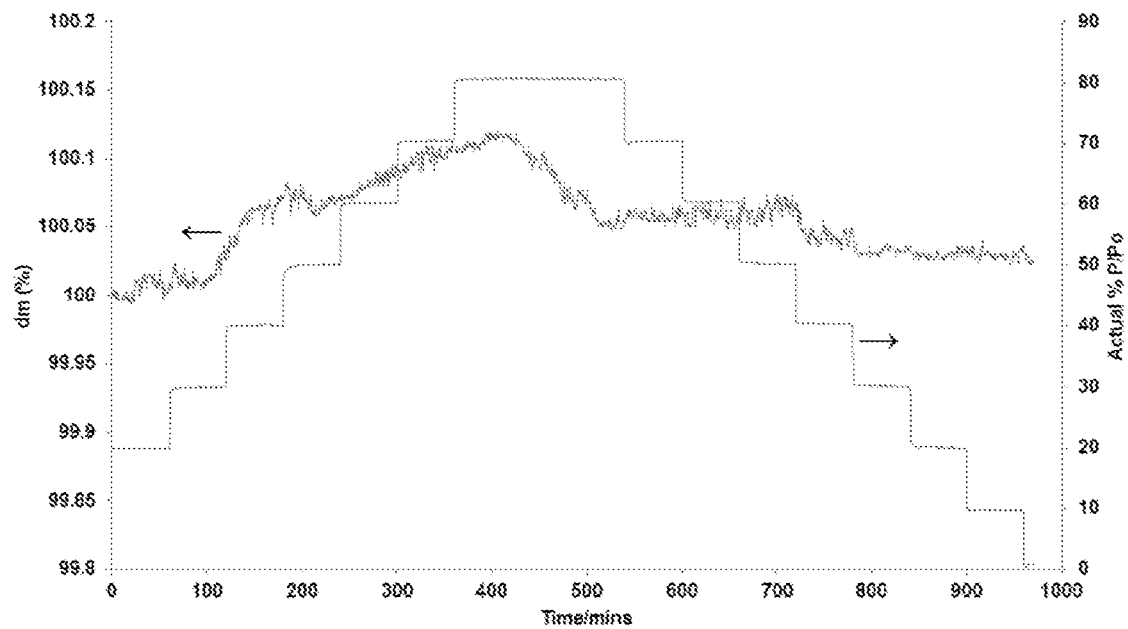

157.2 mg of progesterone and 105.0 mg of 3-nitrophthalic acid were weighed, mixed and placed in an agate mortar, 40 μl of an ethanol-water (volume ratio=1:1) mixed solvent was added dropwise, grinding was then performed, an additional ethanol-water (volume ratio=1:1) mixed solvent was continuously added during the grinding process, and after grinding was performed for 45 min at room temperature, the solution was dried in a vacuum drying cabinet at 65° C. to obtain a cocrystal of progesterone. The obtained cocrystal was subjected to powder X-ray diffraction analysis. Its diffraction pattern is shown in FIG. 3-2, indicating that the obtained crystal is a progesterone-3-nitrophthalic acid cocrystal.

The structure of each of the cocrystals of progesterone prepared in Examples 1-6 was characterized by infrared absorption spectrum, X-ray diffraction and differential scanning calorimetry. The results are shown in the drawings and Table 1.

1. The Results of Infrared Absorption Spectrum

The progesterone monomer, the cocrystal former monomers and the cocrystals of progesterone prepared in Examples 1-6 were analyzed by Fourier infrared spectroscopy. The results are shown in FIGS. 1-1, 2-1 and 3-1. This analysis mainly studied the changes in the stretching vibration frequencies of —C═O and —OH within the range of 1600 to 1710 $cm^{-1}$ and 2500 to 3500 $cm^{-1}$. It is found that after progesterone forms a cocrystal with isophthalic acid, 4-benzeneboronic acid or 3-nitrophthalic acid, due to the effect of hydrogen bonds, the characteristic wave number and waveform within the above wavelength ranges are apparently changed, proving the formation of cocrystals of progesterone.

2. The Results of X-Ray Diffraction

The cocrystals of progesterone prepared in Examples 1-3 were analyzed by single-crystal X-ray diffraction respectively. The crystal data and structural parameters of the cocrystals of progesterone are shown in Table 1 below.

TABLE 1 the crystal data and structural parameters of the cocrystals of progesterone

| | Pro-IPA | Pro-BBA | Pro-NPA |
|---|---|---|---|
| Chemical formula unit | Pro. $0.5(C_8H_6O_4 \cdot H_2O)$ | Pro · $C_7H_7BO_3$ | Pro · $C_8H_5NO_6H_2O$ |
| Empirical formula | $C_{25}H_{34}O_{4.5}$ | $C_{28}H_{37}BO_5$ | $C_{29}H_{37}NO_9$ |
| Formula weight | 406.52 | 464.39 | 543.60 |
| Temperature/K | 296(2) | 296(2) | 296(2) |
| Crystal system | Triclinic | Orthorhombic | Orthorhombic |
| Space group | $P_1$ | $P2_12_12_1$ | $P2_12_12_1$ |
| a/ Å | 21.889(6) | 9.2744(17) | 7.7804(8) |
| b/Å | 7.4735(17) | 14.001(3) | 15.6533(15) |
| c/Å | 16.423(4) | 19.632(4) | 22.414(2) |
| α/° | 90 | 90 | 90 |
| β/° | 125.052(14) | 90 | 90 |
| γ/° | 90 | 90 | 90 |
| Volume/Å$^3$ | 2199.3(9) | 2549.2(8) | 2729.8(5) |
| Z | 4 | 4 | 4 |
| $\rho_{calc}$g/cm$^3$ | 1.228 | 1.215 | 1.323 |
| μ/mm$^{-1}$ | 0.083 | 0.081 | 0.098 |
| F(000) | 880 | 1000 | 1160 |
| Radiation | Mo-Kα | Mo-Kα | Mo-Kα |
| 2θ range /° | 1.51 to 27.51 | 3.35 to 27.50 | 1.59 to 25.44 |
| Index ranges | −28 ≤ h ≤ 28 −9 ≤ k ≤ 9 −20 ≤ l ≤ 21 | −12 ≤ h ≤10 −18 ≤ k ≤ 18 −25 ≤ l ≤ 21 | −8 ≤ h ≤ 9 −18 ≤ k ≤ 18 −27 ≤ l ≤ 23 |
| Reflns collected | 14151 | 17964 | 14423 |
| Unique reflns, Rint | 4693, 0.2434 | 5828, 0.0488 | 5036, 0.0304 |
| Data/restraints/parameters | 4693/5/277 | 5828/0/311 | 5036/3/366 |
| GOF | 0.912 | 0.918 | 1.004 |
| $R_1$ [I > 2(I)] | 0.0677 | 0.0476 | 0.0409 |
| $wR_2$(all) | 0.2780 | 0.1281 | 0.1101 |
| Largest diff. peak/hole/e Å$^{-3}$ | 0.725/−0.801 | 0.144/−0.147 | 0.226/−0.223 |

Single-crystal X-ray diffraction measurement confirmed that the cocrystals of progesterone are formed by bonding progesterone to the cocrystal formers via hydrogen bonds, and belong to pharmaceutical cocrystals.

The progesterone monomer, the cocrystal former monomers and the cocrystals of progesterone prepared in Examples 4-6 were subjected to powder X-ray diffraction analysis. The results are shown in FIGS. 1-2, 2-2 and 3-2. By comparison, the powder X-ray diffraction pattern of the cocrystal of progesterone is significantly different from that of the progesterone monomer and that of the corresponding cocrystal former monomer in such aspects as the number of diffraction peaks, the position of the diffraction peaks, and the intensity of the diffraction peaks, which indicates the cocrystals of progesterone show new diffraction peaks which were obviously different from those of the monomers. The powder X-ray diffraction patterns of the cocrystals of progesterone are consistent with the theoretical patterns (SC simulated) of the cocrystals simulated through software with the crystal data obtained from single-crystal X-ray diffraction, indicating that the obtained cocrystals of progesterone have relatively high crystallinity and purity.

From the results of single-crystal and powder X-ray diffraction, it is clear that each of the cocrystals of progesterone has the following morphological characteristics.

(1) The basic structural unit of the progesterone-isophthalic acid cocrystal is formed by bonding two progesterone molecules and one isophthalic acid molecule together via intermolecular hydrogen bonds, wherein the carbonyl group in the progesterone molecule acts as a hydrogen bond acceptor, and the carboxyl group in the isophthalic acid molecule acts as a hydrogen bond donor. The cocrystal belongs to a triclinic system with a space group of P1 and unit cell parameters of a=21.889(6) Å, b=7.4735(17) Å, c=16.423(4) Å, $\alpha=\gamma=90°$, $\beta=125.052(14)$, V=2199.3(9) Å$^3$ and Z=4. Powder X-ray diffraction characteristic peaks of the progesterone-isophthalic acid cocrystal, expressed as 2θ angles, appear at 6.56°±0.2°, 10.96°±0.2°, 13.14°±0.2°, 16.17°±0.2°, 19.76°±0.2°, 20.32°±0.2°, 21.04°±0.2°, 22.20°±0.2°, 24.17°±0.2°, 26.45°±0.2°, 28.05°±0.2°, and 28.55°±0.2°.

(2) The basic structural unit of the progesterone-4-formylbenzeneboronic acid cocrystal is formed by bonding one progesterone molecule and one 4-formylbenzeneboronic acid molecule together via an intermolecular hydrogen bond, wherein the carbonyl group in the progesterone molecule and the carbonyl group in the 4-formylbenzeneboronic acid molecule act as hydrogen bond acceptors, and the hydroxyl group in the 4-formylbenzeneboronic acid molecule and the six-membered ring in the progesterone molecule act as hydrogen bond donors. The cocrystal belongs to an orthorhombic system with a space group of $P2_12_12_1$, and unit cell parameters of a=9.2744(17)Å, b=14.001(3)Å, c=19.632(4)Å, $\alpha=\beta=\gamma=90°$, V=2549.2(8)Å$^3$ and Z=4. Powder X-ray diffraction characteristic peaks of the progesterone-4-formylbenzeneboronic acid cocrystal, expressed as 2θ angles, appear at 9.04°±0.2°, 10.55°±0.2°, 12.64°±0.2°, 13.44°±0.2°, 16.48°±0.2°, 16.99°±0.2°, 18.22°±0.2°, 19.11°±0.2°, 19.66°±0.2°, 20.70°±0.2°, 21.18°±0.2°, 22.12°±0.2°, 23.48°±0.2°, 24.68°±0.2°, 26.63°±0.2°, and 27.85°±0.2°.

(3) The basic structural unit of the progesterone-3-nitrophthalic acid cocrystal is formed by bonding one progesterone molecule and one 3-nitrophthalic acid molecule together via an intermolecular hydrogen bond, wherein the carbonyl group in the progesterone molecule acts as a hydrogen bond acceptor, and the hydroxyl group in the 4-formylbenzeneboronic acid molecule and the carboxylc group in the 3-nitrophthalic acid molecule acts as hydrogen bond donors. The cocrystal belongs to an orthorhombic system with a space group of $P2_12_12_1$, and unit cell parameters of a=7.7804(8)Å, b=15.6533(15)Å, c=22.414(2)Å, $\alpha=\beta=\gamma=90°$, V=2729.8(5) Å$^3$ and Z=4. Powder X-ray diffraction characteristic peaks of the cocrystal, expressed as 2θ angles, appear at 9.08°±0.2°, 13.01°±0.2°, 13.39°±0.2°, 13.78°±0.2°, 15.88°±0.2°, 16.55°±0.2°, 18.78°±0.2°, 19.29°±0.2°, 20.87°±0.2°, 23.34°±0.2°, 26.27°±0.2°, 27.33°±0.2°, and 29.79°±0.2°.

Figure 8:
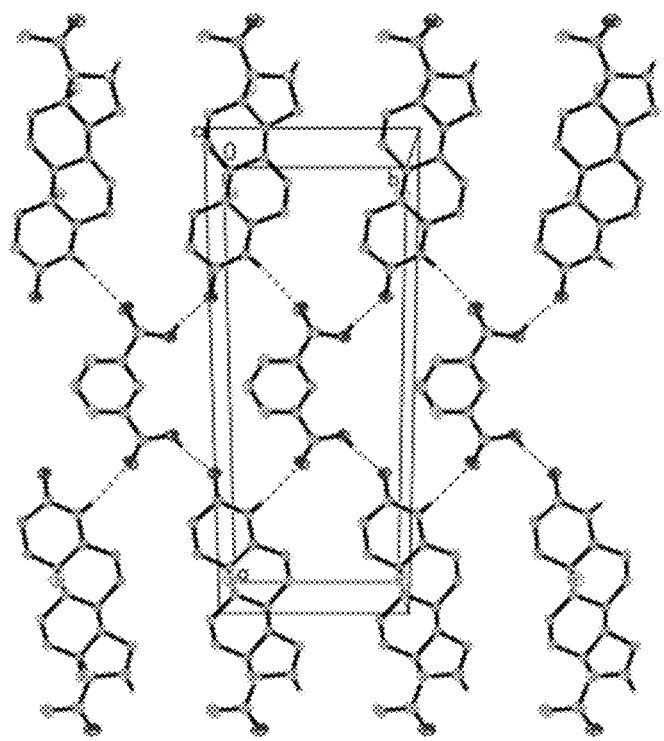
FIG. 8 shows the Pro-IPA mode of bonding via hydrogen bonds in the cocrystals of progesterone.
Figure 9:
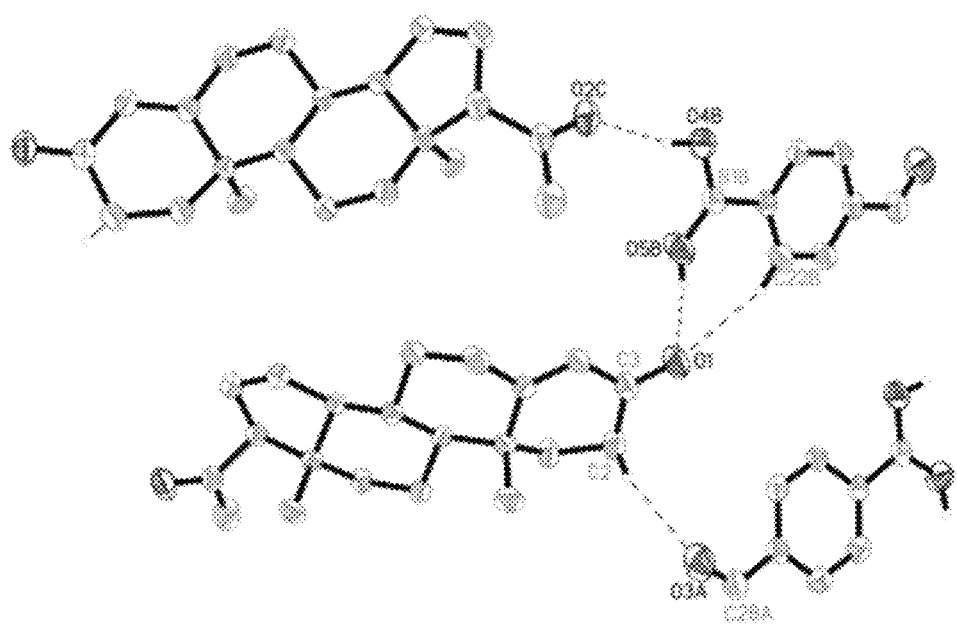
FIG. 9 shows the Pro-BBA mode of bonding via hydrogen bonds in the cocrystals of progesterone.
Figure 10:
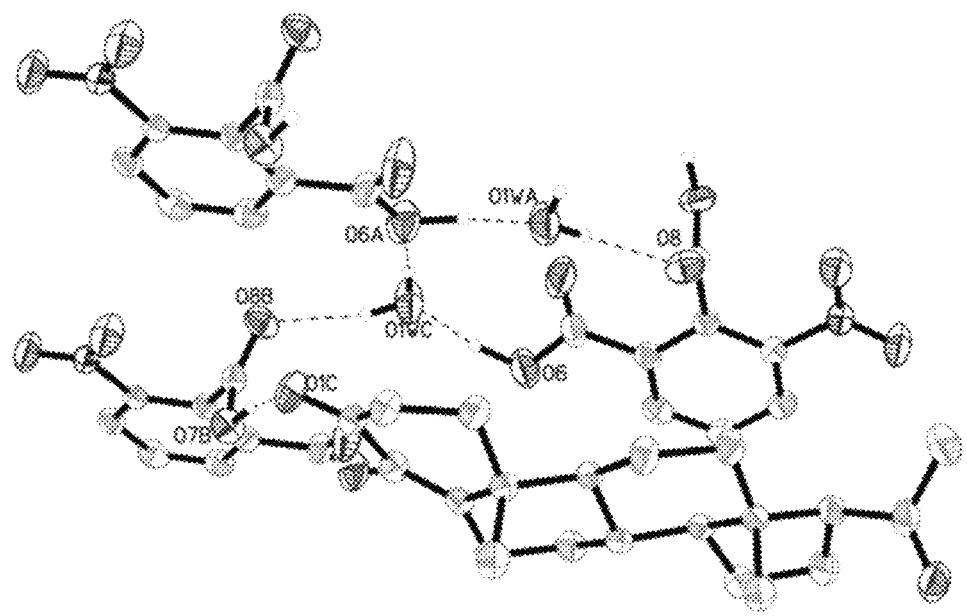
FIG. 10 shows the Pro-NPA mode of bonding via hydrogen bonds in the cocrystals of progesterone.

The modes of bonding via hydrogen bonds in the cocrystals of progesterone are Pro-IPA mode, shown in FIG. 8, Pro-BBA mode, shown in FIG. 9, and Pro-NPA mode, shown in FIG. 10.

3. Results of Differential Scanning Calorimetry

The progesterone monomer, the cocrystal former monomers and the cocrystals of progesterone prepared in Examples 1-6 were analyzed by differential scanning calorimetry at the same heating rate of 10° C./minute. The results, as shown in FIGS. 1-3, 2-3 and 3-3, indicate that the progesterone-isophthalic acid cocrystal has an endothermic peak at 140.1° C.±3° C., and the progesterone-4-formylbenzeneboronic acid cocrystal has an endothermic peak at 114.7° C.±3° C. and the progesterone-3-nitrophthalic acid cocrystal has an endothermic peak at 169.0° C.±3° C. The comparison between the DSC patterns shows that the cocrystals of progesterone are significantly different from the progesterone monomer and the cocrystal former monomers in such aspects as the temperature and position of the endothermic peak, which also indicates the formation of new cocrystals of progesterone.

Example 7 Pharmacodynamic Experiment of Cocrystals of Progesterone

The progesterone-isophthalic acid cocrystal obtained by the method described in the above-mentioned Example 1 was subjected to a pharmacodynamic experiment. Female immature white rabbits were used and randomly divided into blank group, positive control group, low dose group, medium dose group and high dose group, with 10 rabbits in each group. The dose of progesterone that should be given to each rabbit is twice the clinical human dose of progesterone, and is calculated according to the rabbit's body weight. After a solution was prepared from a progesterone-isophthalic acid cocrystal and PBS (containing 0.1% DMSO), the low, medium and high dose groups were injected intramuscularly with 3.5 mg·kg$^{-1}$, 7 mg·kg$^{-1}$ and 14 mg·kg$^{-1}$ of the solution respectively, the blank group was injected intramuscularly with a PBS solution containing 0.1% DMSO, and the positive control group was injected intramuscularly with 14 mg·kg$^{-1}$ of a progesterone injection. The intramuscular injections were performed for a consecutive 30 days. Weighing was performed on day 1 and day 30 respectively. A part of the uterine tissue 2 cm from the junction of the uterus and vagina in the direction of the ovary was cut and weighed. The uterine index was calculated by dividing the weight of the uterus by the weight of each rabbit. The results are shown in Table 2.

TABLE 2

Results of changes in rabbit body weight (kg, x ± s, n = 8) and uterine index (%, x ± s, n = 8)

|  |  | Blank group | Positive control group | Low dose group | Medium dose group | High dose group |
|---|---|---|---|---|---|---|
| Pro-IP A | Day 1 | 0.780 ± 0.114 | 0.820 ± 0.125 | 0.790 ± 0.122 | 0.790 ± 0.132 | 0.830 ± 0.131 |
|  | Day 30 | 1.210 ± 0.162 | 1.290 ± 0.177 | 1.200 ± 0.156 | 1.260 ± 0.200 | 1.390 ± 0.233 |
|  | Uterine index | 0.010 ± 0.001 | 0.074 ± 0.011 | 0.025 ± 0.009 | 0.029 ± 0.009* | 0.035 ± 0.008 |

Note:
as compared with the positive control group, *P < 0.05

After 30 days of administration, rabbits in the positive control group, the blank group, and the low, medium, and high dose groups all had increased body weight. Statistical analysis showed that compared with the blank group, there was no significant difference among the positive control group, and the low, medium and high dose groups. As the dose of progesterone-isophthalic acid cocrystal increased, the uterine index of rabbits showed an increasing trend. The results of statistical analysis showed that there were significant differences in the uterine index among the blank group, the low dose group and the positive control group, and there was no significant difference in the uterine index among the medium dose group, high dose group and the positive control group. This shows that after the administration of the progesterone-isophthalic acid cocrystal, with the increase of the dose, the endometrium thickness increases, and the increase of the uterine index indicates that the progesterone response of rabbits is enhanced. This indicates that the cocrystals of progesterone can be effectively used to protect women's endometrium, prevent miscarriage, and treat menopausal syndrome and thus improve life quality of menopausal women.

Example 8 Determination of the Hygroscopicity of Cocrystals of Progesterone

The progesterone monomer and the cocrystals of progesterone obtained in Examples 1-6 were subjected to dynamic vapour sorption analysis. The nitrogen flow rate was 200 ml/min, and the relative humidity, varied in a stepped manner by a change of 10%, increased from 20% to 80%, and then dropped to 0%. The water sorption kinetic curves at 25° C. were determined, and the results are shown in FIGS. 4, 1-4, 2-4 and 3-4. During the whole process, the change in relative mass of progesterone is less than 0.2%, indicating that progesterone is non-hygroscopic, and will neither absorb water nor be dehydrated when exposed to an environment with a certain humidity level. The changes in relative mass of the cocrystals of progesterone were also less than 0.2%, indicating that the obtained cocrystals of progesterone maintain the non-hygroscopic property of progesterone, and meet the basic requirements for a medicine.

Example 9 Determination of the Dissolution Rate of Cocrystals of Progesterone

Figure 5:
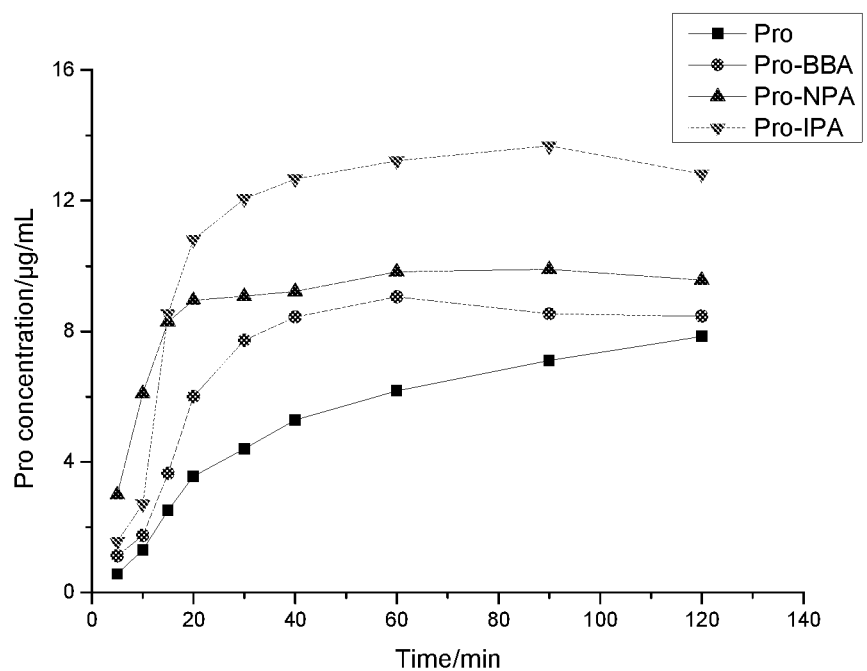
FIG. 5 shows the dissolution curves of the progesterone monomer and three cocrystals of progesterone in water.
Figure 6:
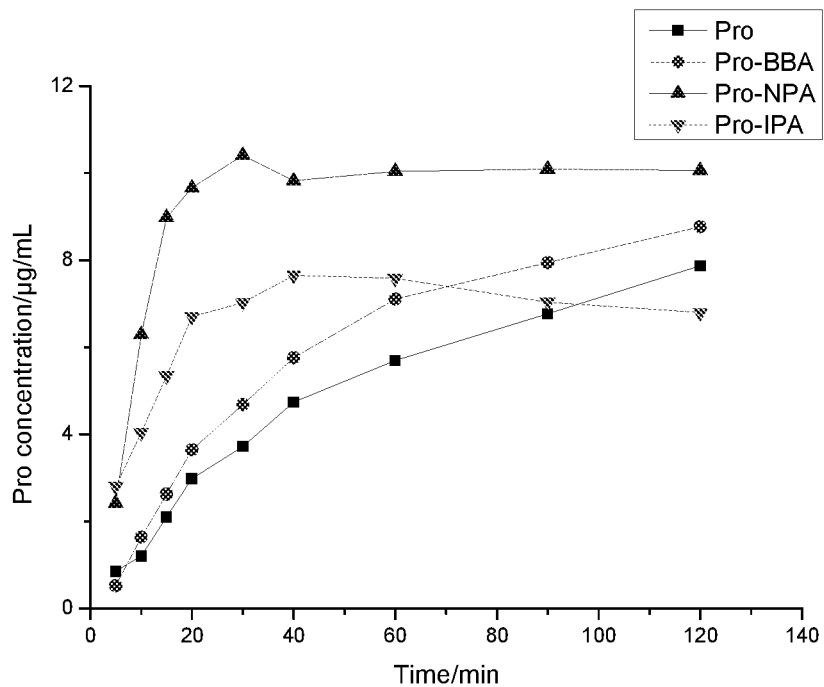
FIG. 6 shows the dissolution curves of the progesterone monomer and three cocrystals of progesterone in a pH 1.2 medium.

The dissolution curves of the progesterone monomer and the cocrystals of progesterone obtained in Examples 1-6 in two dissolution media were measured at 37±0.5° C. and at a rotating speed of 50 to 100 rpm. The two dissolution media are water and pH 1.2 hydrochloric acid solution, respectively. Samples were taken at 5, 10, 15, 20, 30, 40, 60, 90 and 120 min, respectively. The content of progesterone at the wavelength of 241 nm was measured by the HPLC method, and the dissolution amount was calculated by the external standard method. Dissolution curves with time as the abscissa and the concentration of progesterone as the ordinate were respectively plotted, as shown in FIGS. 5 and 6. FIG. 5 shows that the mass concentration of progesterone in water reached the highest value of 7.84 µg/ml at 120 min; the concentration of progesterone in the progesterone-isophthalic acid cocrystal reached the highest value of 13.68 µg/ml at 90 min, that in the progesterone-4-formylbenzeneboronic acid cocrystal reached the highest value of 9.06 µg/ml at 60 min, and that in the progesterone-3-nitrophthalic acid cocrystal reached the highest value of 9.90 µg/ml at 90 min. The solubility of the cocrystals of progesterone in water is 1.7, 1.2, and 1.3 times that of the progesterone monomer. FIG. 6 shows that the mass concentration of progesterone in pH 1.2 hydrochloric acid solution reached the highest value of 7.87 µg/ml at 120 min; the concentration of progesterone in the progesterone-isophthalic acid cocrystal reached the highest value of 7.65 µg/ml at 40 min, that in the progesterone-4-formylbenzeneboronic acid cocrystal reached the highest value of 8.77 µg/ml at 120 min, and that in the progesterone-3-nitrophthalic acid cocrystal reached the highest value of 10.4 µg/ml at 30 min. The solubility of the cocrystals of progesterone in the solution is 1.0, 1.1, and 1.3 times that of the progesterone monomer.

As can be seen from the experimental data, the dissolution behavior of the cocrystals of progesterone according to the present invention in both water and pH 1.2 hydrochloric acid solution is better than that of progesterone. This is specifically embodied in that the cocrystals of progesterone have faster dissolution rates, and thus can be rapidly absorbed to reach effective blood drug concentration, thereby realizing the drug's therapeutic effects.

Example 10 Determination of the Permeation Rate of Cocrystals of Progesterone

The permeation rate and effective permeability of the progesterone monomer and the cocrystals of progesterone obtained in Examples 1-6 during passive transport were determined by parallel artificial membrane permeability assay (PAMPA). Since the pH of fasting intestinal fluid in a human body is 6.5 and the pH of blood is 7.4, in order to make the conditions under which the permeation rate was measured close to the environment of the human gastrointestinal tract, pH 6.8 phosphate buffer was selected as the medium in the experiment. 3 mg of progesterone monomers and cocrystals of progesterone equivalent to 3 mg of progesterone were accurately weighed, and respectively placed in a donor compartment that represents the gastrointestinal tract, and 20 ml of pH 6.8 phosphate buffer was accurately added. 20 ml of pH 7.4 ASB buffer was accurately added to a receptor compartment that represents blood. The two compartments were separated by a biomimetic membrane with an area of 1.54 cm². The biomimetic membrane was coated with 25 μl of simulated gastrointestinal liposomes for infiltration, which represents the cell membrane of the gastrointestinal tract. At the temperature of 37° C. and the stirring speed of 200 rpm, sampling was conducted for 4 h, with an interval of 60 s between each two sampling procedures. The drug concentration in the receptor compartment was measured with a fiber optic probe within the ultraviolet wavelength range of 250 to 350 nm. The artificial membrane permeation rate of the drug was calculated according to Formula 1 (J/Flux). The effective permeability of the drug was calculated according to Formula 2:

$$J = \frac{dc}{dt} \times \frac{V}{A} \quad \text{(Formula 1)}$$

$$Pe = \frac{dc}{dt} \times \frac{V}{A \times Ct \times 60} \quad \text{(Formula 2)}$$

In the formula, J (Flux) represents the permeation rate, i.e. the amount of a drug passing through a unit membrane area per unit time ($\mu g \cdot min^{-1} \cdot cm^{-2}$); Pe represents the effective permeability ($cm \cdot s^{-1}$);

$$\frac{dc}{dt}$$

represents the rate of change of drug concentration in the receptor compartment per unit time ($\mu g \cdot mL^{-1} \cdot min^{-1}$); V is the volume of buffer in the receptor compartment (mL); A is the area of the biomimetic membrane (cm²); and Ct is the initial concentration of the drug in the donor compartment ($\mu g \cdot mL^{-1}$).

Figure 7:
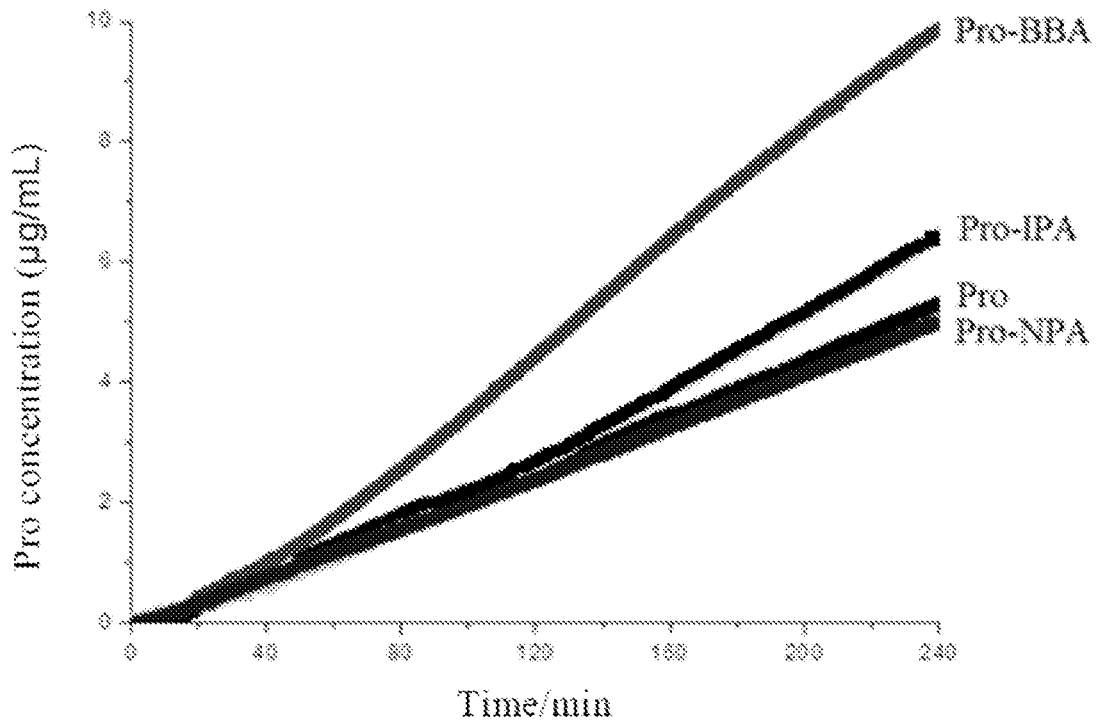
FIG. 7 shows the permeation curves of the progesterone monomer and three cocrystals of progesterone in a pH 6.8 medium.

The permeation curves of progesterone and the cocrystals of progesterone in pH 6.8 phosphate buffer are shown in FIG. 7. As the detection time increases, the drug gradually passed through the simulated gastrointestinal cell membrane and transferred from the donor compartment to the receptor compartment. The level of drug permeability can be determined by comparing the permeability of the drug with that of metoprolol measured by the same method. Drugs whose permeability is higher than that of metoprolol are high-permeability drugs, and whose permeability is lower than that of metoprolol are low-permeability drugs. According to Formula 2, it is calculated that the effective permeability of progesterone is $1.11 \times 10^{-3}$ cm·s$^{-1}$ and the effective permeability of the progesterone-isophthalic acid cocrystal, of the progesterone-4-formylbenzeneboronic acid cocrystal, and of the progesterone-3-nitrophthalic acid cocrystal is $9.38 \times 10^{-4}$, $8.87 \times 10^{-4}$ and $1.46 \times 10^{-3}$ cm·s$^{-1}$, all of which are higher than the permeability of $1.20 \times 10^{-4}$ cm·s$^{-1}$ of metoprolol tartrate measured by the same method. Thus, it can be seen both progesterone and the three cocrystals of progesterone are high-permeability drugs, indicating that after formed, the cocrystals of progesterone maintain the property of high permeability of progesterone. According to Formula 1, it is calculated that the permeation rate of progesterone is 0.32 μg·min$^{-1}$·cm$^{-2}$, and the permeation rate of the progesterone-isophthalic acid cocrystal, of the progesterone-4-formylbenzeneboronic acid cocrystal, and of the progesterone-3-nitrophthalic acid cocrystal is 0.36, 0.62, and 0.28 μg·min$^{-1}$·cm$^{-2}$ respectively, which are 1.1, 1.9 and 0.9 times that of the progesterone monomer, respectively.

The experimental data demonstrate that both progesterone and the progesterone-isophthalic acid cocrystal, the progesterone-4-formylbenzeneboronic acid cocrystal, and the progesterone-3-nitrophthalic acid cocrystal have high permeability, wherein the progesterone-isophthalic acid cocrystal and the progesterone-4-formylbenzeneboronic acid cocrystal have increased permeation rates of progesterone and thus have enhanced bioavailability.

The invention claimed is:

1. A cocrystal of progesterone, characterized in that the cocrystal of progesterone is formed by the active ingredient progesterone and a cocrystal former, which is selected from the group consisting of isophthalic acid, 4-formylbenzeneboronic acid, and 3-nitrophthalic acid;
    wherein when the cocrystal former is isophthalic acid, powder X-ray diffraction characteristic peaks of the resulting progesterone-isophthalic acid cocrystal, expressed as 2θ angles, appear at 6.56°, 10.96°, 13.14°, 16.17°, 19.76°, 20.32°, 21.04°, 22.20°, 24.17°, 26.45°, 28.05°, and 28.55°;
    wherein when the cocrystal former is 4-formylbenzeneboronic acid, powder X-ray diffraction characteristic peaks of the resulting progesterone-4-formylbenzeneboronic acid cocrystal, expressed as 2θ angles, appear at 9.04°, 10.55°, 12.64°, 13.44°, 15.53°, 16.48°, 16.99°, 18.22°, 19.11°, 19.66°, 20.70°, 21.18°, 22.12°, 23.48°, 24.68°, 26.63°, and 27.85°;
    wherein when the cocrystal former is 3-nitrophthalic acid, powder X-ray diffraction characteristic peaks of the resulting progesterone-3-nitrophthalic acid cocrystal, expressed as 2θ angles, appear at 9.08°, 13.01°, 13.39°, 13.78°, 15.88°, 16.55°, 18.78°, 19.29°, 20.87°, 23.34°, 26.27°, 27.33° and 29.79°.

2. The cocrystal of progesterone according to claim 1, characterized in that progesterone and the cocrystal former are present in a molar ratio of 1:3 to 3:1.

3. The cocrystal of progesterone according to claim 1, characterized in that progesterone is connected to the cocrystal former via hydrogen bonds.

4. The cocrystal of progesterone according to claim 1, characterized in that
    (1) wherein when the cocrystal former is isophthalic acid, a progesterone-isophthalic acid cocrystal is obtained, wherein the progesterone-isophthalic acid cocrystal belongs to a triclinic system with a space group of P1 and unit cell parameters of a=21.889(6) Å, b=7.4735 (17) Å, c=16.423(4) Å, α=γ=90°, β=125.052(14), V=2199.3(9) Å³ and Z=4; $\rho_{calc}$g=1.228 cm³; μ=0.083 mm$^{-1}$; F(000)=880; radiation of Mo-Kα; 2θ range of 1.51° to 27.51°; index ranges of −28≤h≤28, −9≤k≤9 and −20≤l≤21; reflections collected=14151; unique reflections, Rint=4693, 0.2434; unique reflections data/restraints/parameters=4693/5/277; goodness-of-fit (GOF)=0.912; R$_1$[I>2(I)]=0.0677; wR$_2$ (all)=0.2780; and largest difference peak/hole=0.725/−0.801 e Å$^{-3}$;
    (2) wherein when the cocrystal former is 4-formylbenzeneboronic acid, a progesterone-4-formylbenzeneboronic acid cocrystal was obtained, wherein the progesterone-4-formylbenzeneboronic acid cocrystal belongs to an orthorhombic system with a space group of P2$_1$2$_1$2$_1$, and unit cell parameters of a=9.2744(17)Å, b=14.001(3)Å, c=19.632(4)Å, α=β=γ=90°, V=2549.2 (8)Å³ and Z=4; $\rho_{calc}$g=1.215 cm³; μ=0.081 mm$^{-1}$; F(000)=1000; radiation of Mo-Kα; 2θ range of 3.35° to 27.50°; index ranges of −12≤h≤10, −18≤k≤18 and −25≤l≤21; reflections collected=17964; unique reflections, Rint=5828, 0.0488; unique reflections data/restraints/parameters=5828/0/311; goodness-of-fit (GOF)=0.918; $R_1[I>2(I)]$=0.0476; $wR_2$ (all)=0.1281; and largest difference peak/hole=0.144/−0.147 e Å$^{-3}$; and (3) wherein when the cocrystal former is 3-nitrophthalic acid, a progesterone-3-nitrophthalic acid cocrystal is obtained, wherein the progesterone-3-nitrophthalic acid cocrystal belongs to an orthorhombic system with a space group of $P2_12_12_1$, and unit cell parameters of a=7.7804(8)Å, b=15.6533(15)Å, c=22.414(2)Å, α=β=γ=90°, V=2729.8(5)Å$^3$ and Z=4; $ρ_{calc}$g=1.323 cm$^3$; μ=0.098 mm$^{-1}$; F(000)=1160; radiation of Mo-Kα; 2θ range of 1.59° to index ranges of −8≤h≤9, −18≤k≤18 and −27≤l≤23; reflections collected=14423; unique reflections, Rint=5036, 0.0304; unique reflections data/restraints/parameters=5036/3/366; goodness-of-fit (GOF)=1.004; $R_1[I>2(I)]$=0.0409; $wR_2$(all) =0.1101; and largest difference peak/hole=0.226/−0.223 e Å$^{-3}$.

5. A method for preparing the cocrystal of progesterone according to claim 1, characterized in that the method comprises the following steps: mixing progesterone and the cocrystal former in proportion, adding a solvent and stirring at 0 to 80° C. for 30 to 360 min until a completely clear solution is obtained, then allowing the solution to stand at room temperature for 3 to 15 days to volatilize the solvent and precipitate crystals, and obtaining a cocrystal of progesterone after filtrating and drying.

6. The method according to claim 5, characterized in that the temperature is 10° C. to 70° C.

7. The method according to claim 5, characterized in that the solvent is one of or a mixture of more than one of methanol, ethanol, n-propanol, n-butanol, isopropanol, tert-butanol, n-hexanol, ethylene glycol, acetonitrile, acetone, n-hexane, or water, wherein progesterone and the cocrystal former are present in a molar ratio of 1:3 to 3:1.

8. A method for preparing the cocrystal of progesterone according to claim 1, characterized in that the method comprises the following steps: mixing progesterone and the cocrystal former in proportion and placing them in a mortar, adding a solvent dropwise and performing grinding, continuously adding an additional solvent during grinding, and after grinding for 10 to 300 min at a temperature of 10° C. to 50° C., performing drying in a vacuum drying cabinet at 40° C. to 80° C. to obtain a cocrystal of progesterone.

9. The method according to claim 8, characterized in that the temperature during grinding is 15° C. to 45° C.; the grinding time is 30 to 260 min; and the temperature in the vacuum drying cabinet is 45° C. to 75° C.

10. The method according to claim 8, characterized in that solvent is one of or a mixture of more than one of methanol, ethanol, n-propanol, n-butanol, isopropanol, tert-butanol, n-hexanol, ethylene glycol, acetonitrile, acetone, n-hexane, or water, wherein progesterone and the cocrystal former are present in a molar ratio of 1:3 to 3:1.

11. A method for increasing endometrium thickness, improving progesterone's solubility or increasing progesterone's permeation rate comprising administering an effective amount of the cocrystal of progesterone of claim 1 to a patient in need of such cocrystal of progesterone.

* * * * *